(12) United States Patent
Sklar

(10) Patent No.: US 6,685,709 B2
(45) Date of Patent: Feb. 3, 2004

(54) APPARATUS AND METHOD FOR RECONSTRUCTING LIGAMENTS

(76) Inventor: Joseph H. Sklar, 210 Park Dr., Longmeadow, MA (US) 01106

(*) Notice: Subject to any disclaimer, the term of this patent is extended or adjusted under 35 U.S.C. 154(b) by 0 days.

(21) Appl. No.: 10/114,659

(22) Filed: Apr. 2, 2002

(65) Prior Publication Data

US 2002/0173795 A1 Nov. 21, 2002

Related U.S. Application Data

(63) Continuation of application No. 09/379,997, filed on Aug. 24, 1999, now Pat. No. 6,364,886, which is a continuation of application No. 09/083,889, filed on May 22, 1998, now Pat. No. 5,941,883, which is a continuation of application No. 08/658,003, filed on Jun. 4, 1996, now Pat. No. 5,755,718.

(51) Int. Cl.[7] ............................................. A61B 17/00
(52) U.S. Cl. ........................... 606/80; 606/88; 606/170; 606/180
(58) Field of Search ....................... 606/78, 79, 80, 606/84, 85, 88, 170, 171, 172, 180

(56) References Cited

U.S. PATENT DOCUMENTS

| | | | |
|---|---|---|---|
| 2,429,356 A | 10/1947 | Hicks | 32/29 |
| 4,445,509 A | 5/1984 | Auth | |
| 5,112,335 A | 5/1992 | Laboureau et al. | 606/88 |
| 5,112,337 A | 5/1992 | Paulos et al. | 606/96 |
| 5,122,134 A | 6/1992 | Borzone et al. | 606/80 |
| 5,234,435 A | 8/1993 | Seagrave, Jr. | 606/103 |
| 5,242,460 A | 9/1993 | Klein et al. | 606/159 |
| 5,269,786 A | 12/1993 | Morgan | 606/96 |
| 5,372,599 A | 12/1994 | Martins | 606/75 |
| 5,374,269 A | 12/1994 | Rosenberg | 606/80 |
| 5,383,884 A | 1/1995 | Summers | 606/170 |
| 5,458,602 A | 10/1995 | Goble et al. | 606/96 |
| 5,464,407 A | 11/1995 | McGuire | 606/86 |
| 5,562,669 A | 10/1996 | McGuire | 606/72 |
| 5,593,416 A | 1/1997 | Donahue | 606/170 |
| 5,601,561 A | 2/1997 | Terry et al. | 606/85 |

OTHER PUBLICATIONS

Howell, Stephen M. et al. "A rationale for predicting anterior cruciate graft impingement by the intercondylar roof", The American Journal of Sports Medicine, vol. 19, No. 3, pp. 276–282.

Morgan, Craig D. et al., "Definitive Landmarks for Reproducible Tibial Tunnel Placement in Anterior Cruciate Ligament Reconstruction", The Journal of Arthoscopic and Related Surgery, vol. 11, No. 3, (Jun.), 1995, pp. 275–288.

Yaru et al., "The effect of tibial attachment site on impingement in an anterior cruciate ligament reconstruction", The American Journal of Sports Medicine, vol. 20, No. 2, pp. 217–220.

(List continued on next page.)

Primary Examiner—David O. Reip
(74) Attorney, Agent, or Firm—Pandiscio & Pandiscio

(57) ABSTRACT

Apparatus for removing bone from a femoral notch, or the like, which includes a guidewire and a router assembly. The router assembly comprises a cutting head fixed to a shaft rotatably disposed in a hole through a body portion of a shield assembly. A hood portion of the shield assembly extends from the body portion of the shield assembly and covers a first portion of the cutting head while leaving exposed a second portion of the cutting head. The guidewire extends through a hole in the shaft, a hole in the cutting head, and a hole in the shield assembly hood portion, such that the router assembly is movable along the guidewire. The shaft is rotatable in the shield assembly body portion such that the second portion of the cutting head is engageable with the bone and operative to remove portions of the bone. The guidewire is installed in the knee so that it extends along the length to be occupied by a graft ligament. The guidewire and router assembly are flexible so that the bone-trimming operation may be conducted dynamically as the knee is moved through a range of natural motions.

1 Claim, 20 Drawing Sheets

OTHER PUBLICATIONS

Howell et al., "Tibial Tunnel Placement in Arterior Cruciate Ligament Reconstruction and Graft Impingement", Clinical Orthopaedics and Related Research, No. 283, Oct. 1992, pp. 187–195.

Johnson et al., "The Arthoscopic "Inpingement Test" During Anterior Cruciate Ligament Reconstruction", The Journal of Arthoscopic and Related Surgery 9(6), 1993, pp. 714–717.

Howell et al., "Failure of Reconstruction of the Anterior Cruciate Ligament Due to Impingement by the Intercondylar Roof", The Journal of Bone and Joint Surgery, Incorporated, Jul. 1993, vol. 75–A, No. 7, pp. 1044–1055.

Lane, John G. et al, Graft Impingement After Anterior Cruciate Ligament Reconstruction, The American Journal of Sports Medicine, vol. 22, No. 3, 415–417.

Berns et al., "Roofplasty requirements in virto for different tibial hole placements in anterior cruciate ligament reconstruction", The American Journal of Sports Medicine, 1993, vol. 21, No. 2, pp. 292–298.

Friedman, et al., "Topographical Anatomy of the Intercondylar Roof—A Pilot Study", Clinical Orthopaedics and Related Research, Sep. 1994, No. 306, pp. 163–170.

Scuderi, "The Femoral Intercondylar Roof Angle: A Reference for Tibial Tunnel Placement in Anterior Cruciate Ligament Reconstruction", Contemporary Orthopaedics, Nov. 1994, vol. 29, No. 5, pp. 317–325.

Melby, "Prep of the NOTCH for ACL Reconstruction", 4 pages, undated.

Graf, "What The Experts Learned—Scientific Session: ACL", Inside AANA, 1 page, undated.

Watanabe et al., "Arthroscopic Findings Associated with Roof Impingement of an Anterior Cruciate Ligament Graft", The American Journal of Sports Medicine, 1995, vol. 23, No. 5, pp. 616–625.

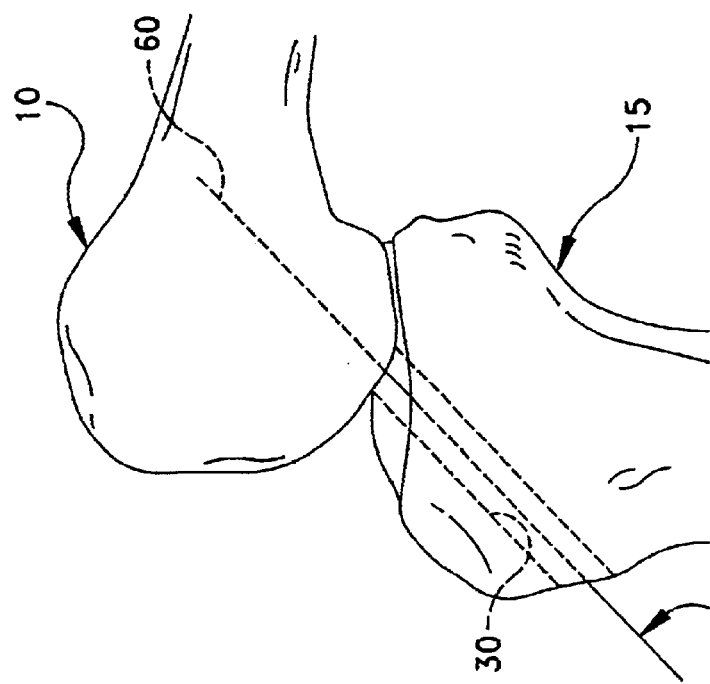
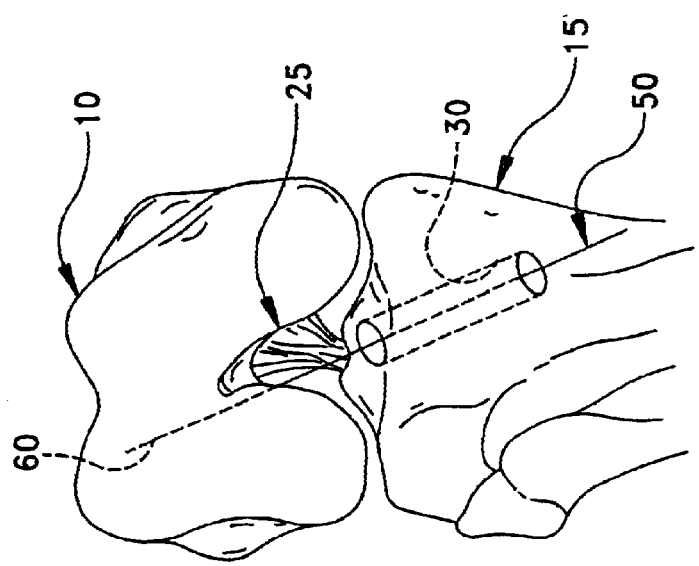

APPARATUS AND METHOD FOR RECONSTRUCTING LIGAMENTS

This is a continuation of U.S. patent application Ser. No. 09/379,997, filed Aug. 24, 1999, now U.S. Pat. No. 6,364,886, which is in turn a continuation of prior application Ser. No. 09/083,889, filed May 22, 1998, now U.S. Pat. No. 5,941,883, which is in turn a contiuation of prior applicaiton Ser. No. 08/658,003, filed Jun. 4, 1996, now U.S. Pat. No. 5,755,713.

FIELD OF THE INVENTION

This invention relates to medical apparatus and methods in general, and more particularly to apparatus and methods for reconstructing ligaments.

BACKGROUND OF THE INVENTION

Ligaments are tough bands of tissue which serve to connect the articular extremities of bones, or to support or retain organs in place within the body. Ligaments are typically composed of coarse bundles of dense white fibrous tissue which are disposed in a parallel or closely interlaced manner, with the fibrous tissue being pliant and flexible, but not extensible.

In many cases, ligaments are torn or ruptured as a result of accidents. As a result, various procedures have been developed to repair or replace such damaged ligaments.

For example, in the human knee, the anterior and posterior cruciate ligaments (i.e., the ACL and PCL) extend between the top end of the tibia and the bottom end of the femur. The ACL and PCL cooperate, together with other ligaments and soft tissue, to provide both static and dynamic stability to the knee. Often, the anterior cruciate ligament (i.e., the ACL) is ruptured or torn as a result of, for example, a sports-related injury. Consequently, various surgical procedures have been developed for reconstructing the ACL so as to restore normal function to the knee.

In many instances, the ACL may be reconstructed by replacing the ruptured ACL with a synthetic or harvested graft ligament. More particularly, with such procedures, bone tunnels are typically formed in the top end of the tibia and the bottom end of the femur, with one end of the graft ligament being positioned in the femoral tunnel and the other end of the graft ligament being positioned in the tibial tunnel. The two ends of the graft ligament are anchored in place in various ways well known in the art so that the graft ligament extends between the femur and the tibia in substantially the same way, and with substantially the same function, as the original ACL. This graft ligament then cooperates with the surrounding anatomical structures so as to restore normal function to the knee.

It will, of course, be appreciated that a complex interdependency exists between the ACL and the other elements of the knee, e.g., the bones, the other knee ligaments, and other soft tissue. Consequently, it is critical that the craft ACL be disposed in exactly the right position relative to the other anatomical structures of the knee if normal knee function is to be restored. Correspondingly, it has been found that the aforementioned bone tunnels must be precisely positioned in the tibia and femur if successful reconstruction of the ACL is to be achieved. Unfortunately, proper positioning of these bone tunnels to satisfy isometric considerations can sometimes lead to anatomical conflicts within the knee when the graft ACL is installed within the knee.

More particularly, the ACL normally extends between the bottom end of the femur and the top end of the tibia, with the body of the ACL passing through the femur's intercondylar notch and across the interior of the knee joint. See, for example, FIGS. 1 and 2, which show a natural ACL 5 extending between the bottom end of a femur 10 and the top end of a tibia 15, with the body of ACL 5 passing through the femur's intercondylar notch 20. Also shown is a natural PCL 25 extending between the bottom end of femur 10 and the top end of tibia 15.

It is to be appreciated that the position of the various knee elements move relative to one another as the knee is flexed through a range of natural motions. See, for example, FIG. 3, which shows ACL 5 moving across a 40° arc as the knee joint is flexed through a 140° motion.

Due to the complex geometries of the knee, where a damaged ACL is to be replaced by a graft ACL, it is critical that the graft ACL be connected at precisely the right locations on the bottom end of the femur and top end of the tibia. Thus, and looking now at FIGS. 4 and 5, where a damaged ACL is to be replaced by a graft ACL, the damaged ACL is first cleared away and then bone tunnels 30 and 35 are formed in the tibia and femur, respectively. The precise locations of these bone tunnels 30 and 35 are dictated by the isometric relationships of the knee. In practice, bone tunnels 30 and 35 are formed using a surgical drill guide which is keyed to certain parts of the patient's anatomy, e.g., to the patient's tibial plateau. Once bone tunnels 30 and 35 have been formed, the graft ACL may be installed in ways well known in the art. See, for example, FIGS. 6 and 7, which show a graft ACL 5A having one end mounted to femur 10 and the other end mounted to tibia 15.

Unfortunately, in some situations, proper isometric placement of bone tunnels 30 and 35 may cause anatomical conflicts within the knee when the graft ACL is installed in the patient. By way of example, and of particular interest in connection with the present invention, proper isometric placement of bone tunnels 30 and 35 may result in portions of the femur impinging upon the graft ACL as the knee is moved through its full range of natural motions. See, for example, FIG. 8, which shows one of the femur's condyles 40 impinging upon a graft ACL 5A extending through the femur's intercondylar notch 20; and FIG. 9, which shows the roof the femur's intercondylar notch impinging on the graft ACL 5A in the vicinity of arrow 42.

Impingement can occur for a variety of reasons. For one thing, the intercondylar notch of many patients (particularly those who are susceptible to rupture of the ACL) is frequently small to begin with. For another thing, the graft ACL (i.e., the synthetic or harvested graft ligament which is being installed in place of the damaged natural ACL) is generally fairly large.

Additionally, slight mispositioning of bone tunnels 30 and 35 can also lead to impingement problems.

Unfortunately, impingement of the femur on the graft ligament can reduce the effectiveness of the ACL reconstruction procedure or even cause it to fail altogether.

Thus, when performing an ACL reconstruction procedure, the surgeon generally tries to ensure that there is sufficient room within the patient's intercondylar notch to receive the graft ligament. This is generally done by performing notchplasty, i.e., by surgically removing any impinging bone from the sides and/or roof of the intercondylar notch. At the same time, of course, it is also important that the surgeon remove no more bone than is absolutely necessary, so as to minimize trauma to the patient.

Unfortunately, it is difficult for the surgeon to accurately gauge the precise amount of bone that must be removed from the notch in order to avoid impingement. For one thing, the ACL reconstruction procedure is typically performed arthroscopically, so that the surgeon's view of the surgical site is frequently fairly restricted. For another thing, the surgeon typically will not know the precise space that the graft ACL will occupy until the graft is actually in place; but at that point in the procedure, it is frequently difficult to insert additional bone-cutting instruments into the joint so as to remove more bone, particularly without cutting the graft ACL. Furthermore, experience has shown that the most serious problems with impingement occur superiorly; but even with the graft ligament in place, the surgeon is generally unable to see impingement at this location due to limitations in arthroscopic visualization. Also, the surgeon typically performs the ACL reconstruction procedure in a relatively static context, i.e., with the knee being relatively stationary at any given moment during the reconstruction procedure. However, the knee must perform (and impingement must be avoided) in a relatively dynamic context, i.e., as the knee is moved throughout a full range of natural motions. This complicates the surgeon's task of eliminating impingement.

OBJECTS OF THE INVENTION

Accordingly, one object of the present invention is to provide improved apparatus for reconstructing a ligament.

Another object of the present invention is to provide improved apparatus for reconstructing an anterior cruciate ligament (ACL).

And another object of the present invention is to provide improved apparatus for quickly, easily and reliably eliminating impingement problems when reconstructing an anterior cruciate ligament.

Still another object of the present invention is to provide improved apparatus for quickly, easily and reliably removing any anatomical structures (e.g., bone) which will conflict with the location of a graft ACL at the completion of an ACL reconstruction procedure.

Yet another object of the present invention is to provide improved apparatus for quickly, easily and reliably removing any anatomical structures (e.g., bone) which will conflict with the location of a graft ACL as the knee is moved through a full range of natural motions.

And an object of the present invention is to provide an improved method for reconstructing a ligament.

Another object of the present invention is to provide an improved method for reconstructing an anterior cruciate ligament (ACL).

And another object of the present invention is to provide an improved method for quickly, easily and reliably eliminating impingement problems when reconstructing an anterior cruciate ligament.

Still another object of the present invention is to provide an improved method for quickly, easily and reliably removing any anatomical structures (e.g., bone) which will conflict with the location of a graft ACL at the completion of an ACL reconstruction procedure.

Yet another object of the present invention is to provide an improved method for quickly, easily and reliably removing any anatomical structures (e.g., bone) which will conflict with the location of a graft ACL as the knee is moved through a full range of natural motions.

SUMMARY OF THE INVENTION

These and other objects are addressed by the present invention, which comprises the provision and use of novel apparatus for removing impinging bone during a ligament reconstruction procedure.

In one preferred form of the invention, the novel apparatus comprises a guidewire and a router assembly.

The guidewire is similar to other guidewires of the sort well known in the art, except that it is preferably formed out of a pseudoelastic material, i.e., a "shape memory alloy (SMA)/stress induced martensite (SIM)" material such as Nitinol.

The router assembly comprises a cannulated router device and a shield assembly. The cannulated router device comprises a cannulated cutting head which is attached to a cannulated shaft. The shield assembly comprises a body and a hood. The body includes a hole therein. The hood extends about one end of the body. The router assembly is assembled so that the router device has its cutting head disposed at one end of the shield assembly's body and the router device has its shaft extending through the hole in the shield assembly's body. The shield assembly's hood covers a first portion of the router device's cutting head while leaving a second portion of the cutting head exposed.

The guidewire is deployed in the body so that it extends along the length where the graft ACL will reside. The router assembly is mounted on the guidewire by passing the guidewire through the router device's shaft and cutting head, such that the router assembly is movable along the guidewire. The router device's shaft is rotatable in the shield assembly such that the cutting head can be turned so as to remove bone while the router assembly is riding on the guidewire. Portions of the router assembly engaging the guidewire are formed so as to be flexible. On account of the fact that both the guidewire and portions of the router assembly are formed so as to be flexible, the router assembly can be used to remove impinging bone as the knee is flexed through a full range of natural motions.

In accordance with another form of the invention, there is provided alternative apparatus for removing impinging bone, the alternative apparatus comprising a guidewire and a cannulated router device. Again, the guidewire is preferably formed out of a pseudoelastic material. The cannulated router device comprises a cannulated cutting head which is attached to a cannulated shaft. In this embodiment of the invention, the cutting head is devoid of cutting means on a first portion of the periphery thereof and is provided with cutting means on a second portion of the periphery thereof. The second portion of the cutting head is engageable with the impinging bone portions which are to be removed.

Again, the guidewire is deployed in the body so that it extends along the length where the graft ACL will reside. The router device is mounted on the guidewire by passing the guidewire through the router device's shaft and cutting head, such that the router device is movable on the guidewire. The router device is rotatably movable in an oscillating fashion such that the cutting head's second portion moves in alternating opposite directions across the impinging bone to remove portions thereof. The first portion of the cutting head is smooth and non-destructive with respect to any anatomical structures which the first portion may come into contact with. Portions of the router device engaging the guidewire are formed so as to be flexible. On account of the fact that both the guidewire and portions of the router device are formed so as to be flexible, the router device can be used to remove impinging bone as the knee is flexed through a full range of natural motions.

In accordance with another form of the invention, there is provided alternative apparatus for removing impinging bone, the alternative apparatus comprising a guidewire and a cannulated router device. Again, the guidewire is preferably formed out of a pseudoelastic material. The cannulated router device comprises a cannulated cutting head which is attached to a cannulated shaft. In this embodiment of the invention, the cutting head is adapted to cut bone which comes into contact with the cutting head, but to leave unharmed soft tissue which comes into contact with the cutting head.

Again, the guidewire is deployed in the body so that it extends along the length where the ACL graft will reside. The router device is mounted on the guidewire by passing the guidewire through the router device's shaft and cutting head, such that the router device is movable on the guidewire. The router device is rotatably movable on the guidewire so as to cut away impinging bone. Again, portions of the router device engaging the guidewire are formed so as to be flexible. On account of the fact that both the guidewire and portions of the router device are formed so as to be flexible, the router device can be used to remove impinging bone as the knee is flexed through a full range of natural motions.

In accordance with another form of the invention, there is provided apparatus for marking portions of impinging bone which are to be thereafter removed, the apparatus comprising a guidewire and a cannulated marking device. Again, the guidewire is preferably formed out of a pseudoelastic material. The cannulated marking device comprises a cannulated marker head attached to a cannulated shaft.

Again, the guidewire is deployed in the body so that it extends along the length where the graft ACL will reside. The marking device is mounted on the guidewire by passing the guidewire through the marking device's shaft and marking head, such that the marking head is movable on the guidewire. The marking head is adapted to hold a dye and to release that dye upon contact with bone, whereby to mark the impinging portions of the bone proximate to the guidewire as the marking head moves on the guidewire. Portions of the marking device engaging the guidewire are formed so as to be flexible. On account of the fact that both the guidewire and portions of the marking device are formed so as to be flexible, the marking device can be used to mark impinging bone as the knee is flexed through a full range of natural motions.

In accordance with a further feature of the invention, there is provided a method for removing impinging portions of bone, the method comprising the steps of providing a flexible guidewire and a flexible cannulated router device. The guidewire is anchored in the bone so that it extends along the length where the graft ACL will reside, and the cannulated router device is rotatably mounted on the guidewire so that it is movable on the guidewire. Then the cannulated router device is rotated on the guidewire as the knee is flexed through a range of natural motions so as to dynamically remove impinging bone.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts and further wherein:

FIG. 17 is a schematic side view of a knee, where the knee is bent at approximately a 90° angle, and where a damaged ACL has been removed and a bone tunnel has been formed in the tibia, and showing a guidewire extending through the tibial bone tunnel and into the femur;

FIG. 18 is a schematic side view of the knee shown in FIG. 17;

DETAILED DESCRIPTION OF THE PREFERRED EMBODIMENTS

Figure 1:
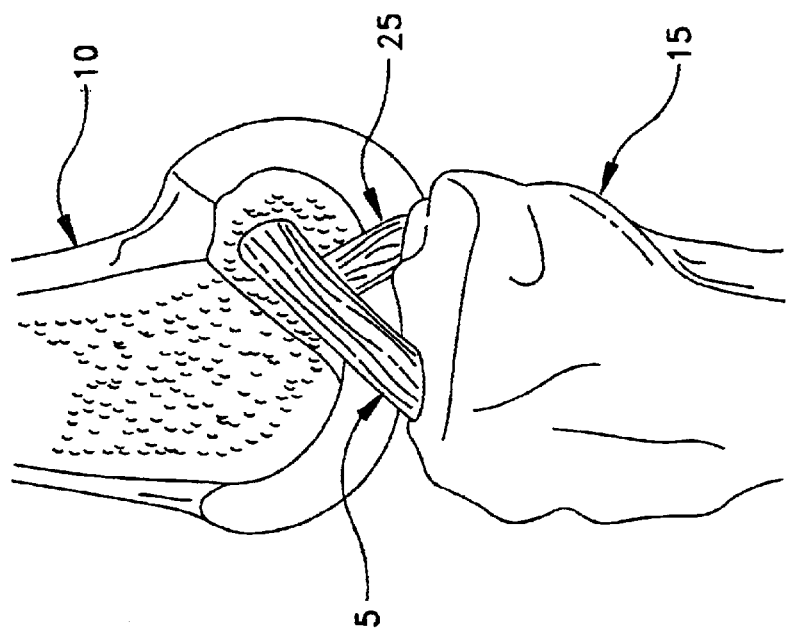
FIG. 1 is a schematic front view of a normal knee, where the leg is substantially straight.
Figure 2:
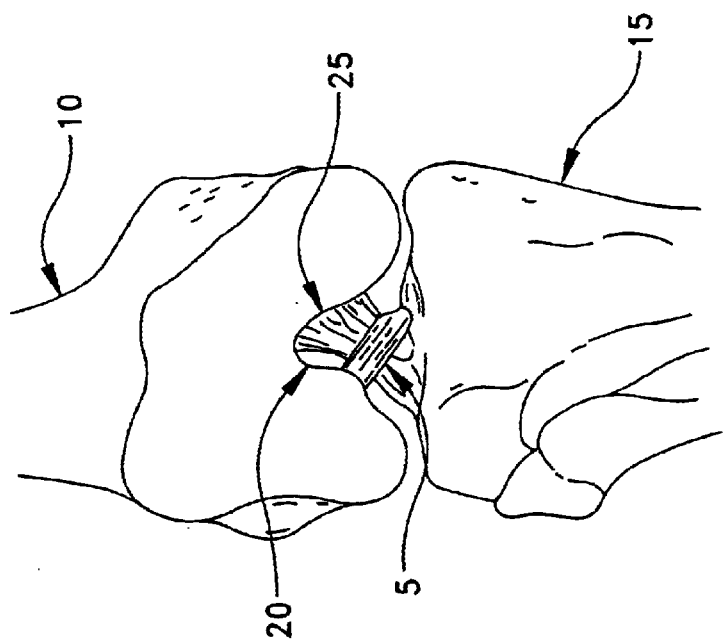
FIG. 2 is a schematic side view, partially in section, of the knee shown in FIG. 1.
Figure 3:
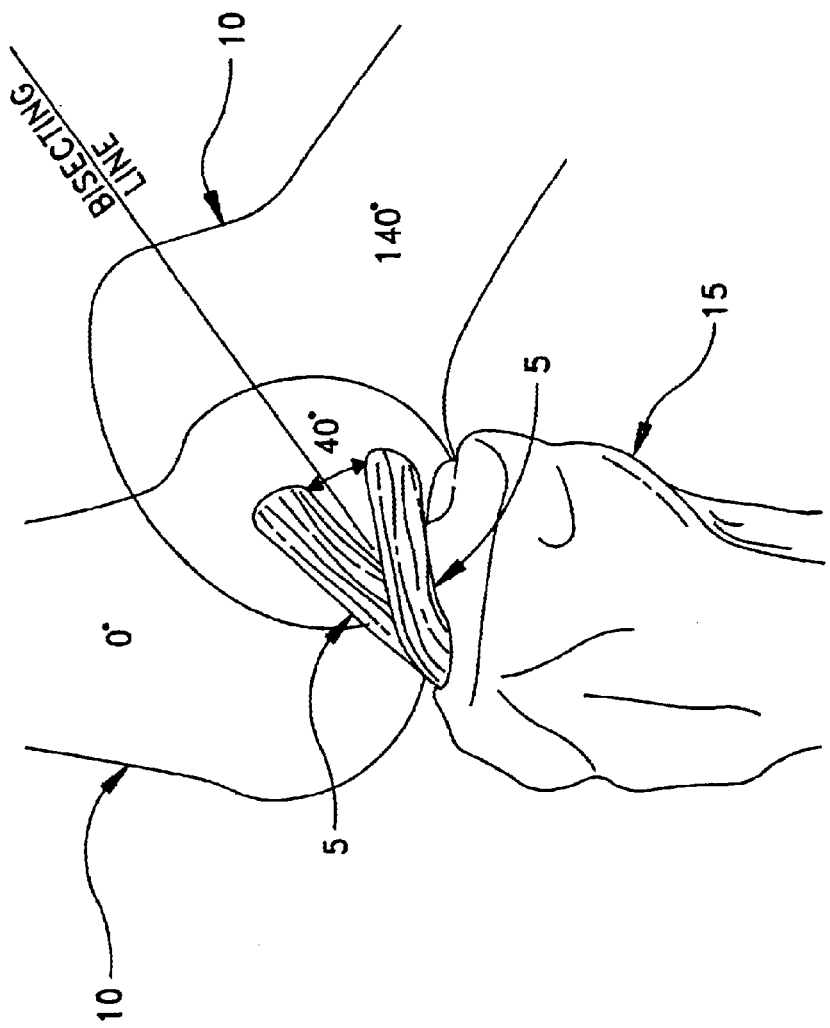
FIG. 3 is a schematic side view, showing how the ACL moves about within the knee joint as the knee is flexed through a range of natural motions.
Figure 5:
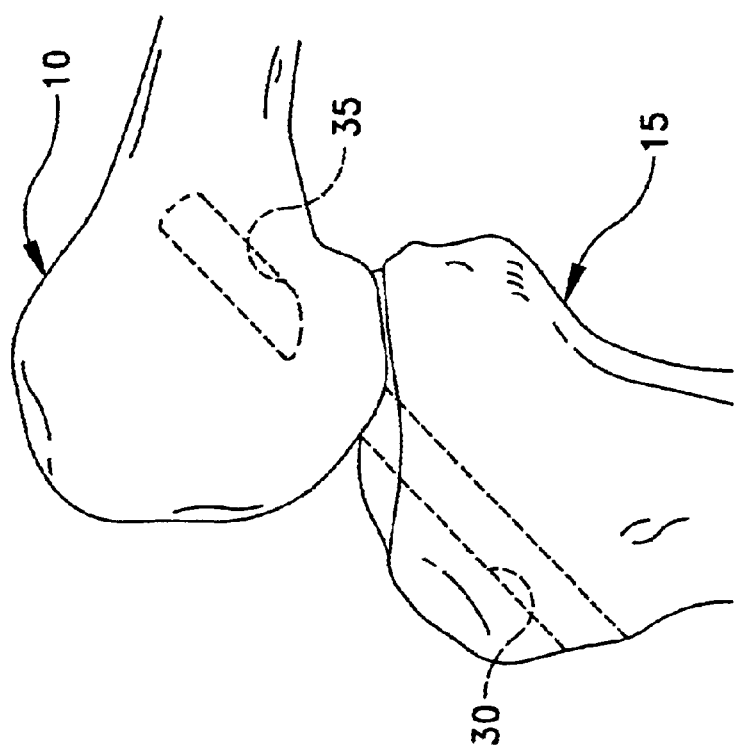
FIG. 5 is a schematic side view of the knee shown in FIG. 4.
Figure 4:
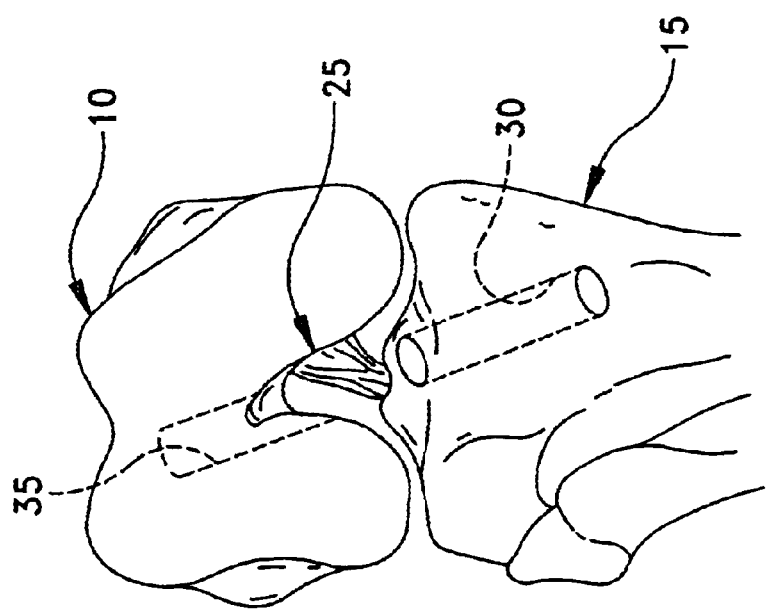
FIG. 4 is a schematic front view of a knee, where the knee is bent at approximately a 90° angle, and where a damaged ACL has been removed and bone tunnels have been formed in the tibia and the femur.
Figure 7:
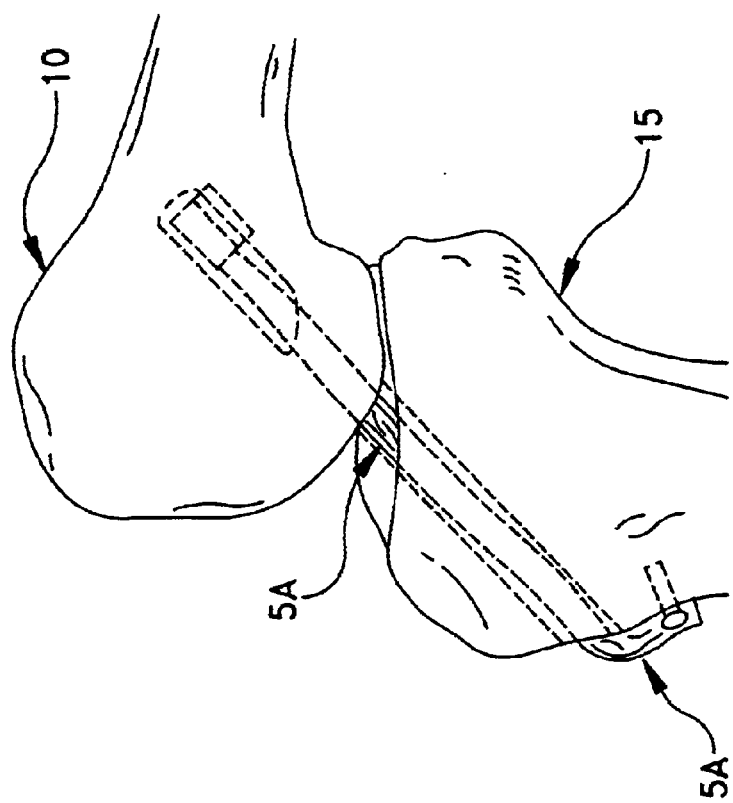
FIG. 7 is a schematic side view of the knee shown is FIG. 6.
Figure 6:
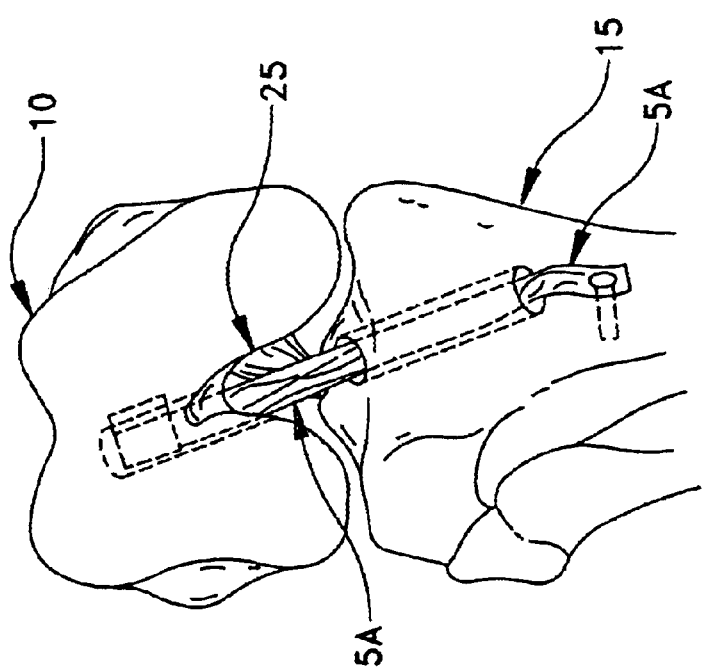
FIG. 6 is a schematic front view of a knee, where the knee is bent at approximately a 90° angle, showing a graft ACL installed in the knee.
Figure 9:
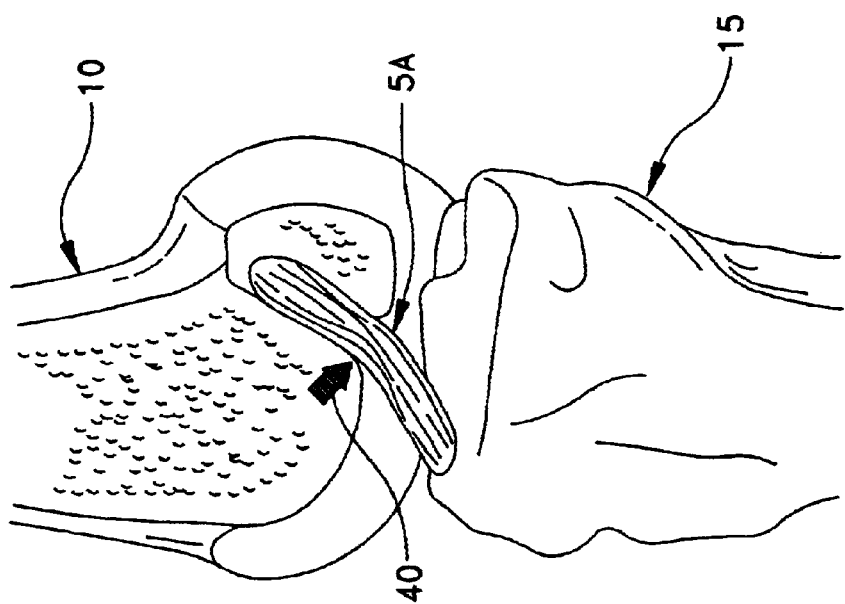
FIG. 9 is a schematic side view showing how portions of the femur can impinge upon a graft ACL.
Figure 8:
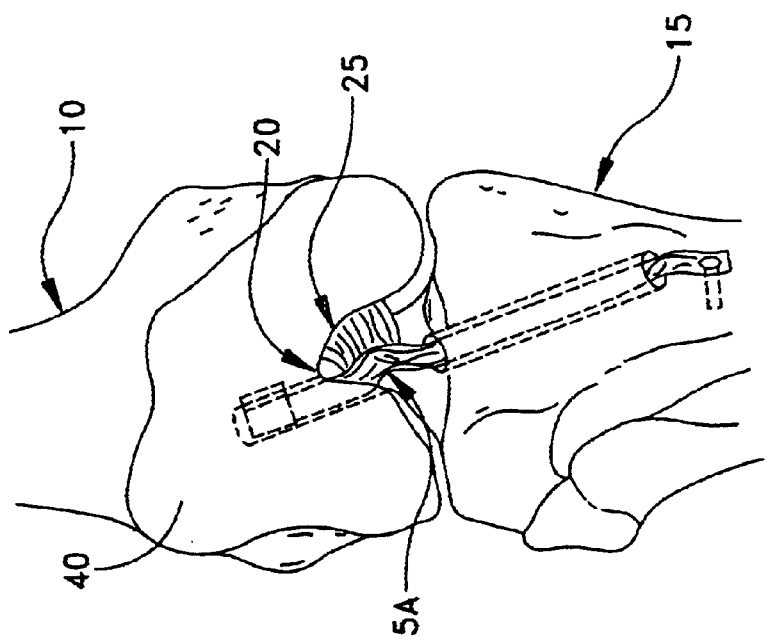
FIG. 8 is a schematic front view showing how portions of the femur can impinge upon a craft ACL.
Figure 10:
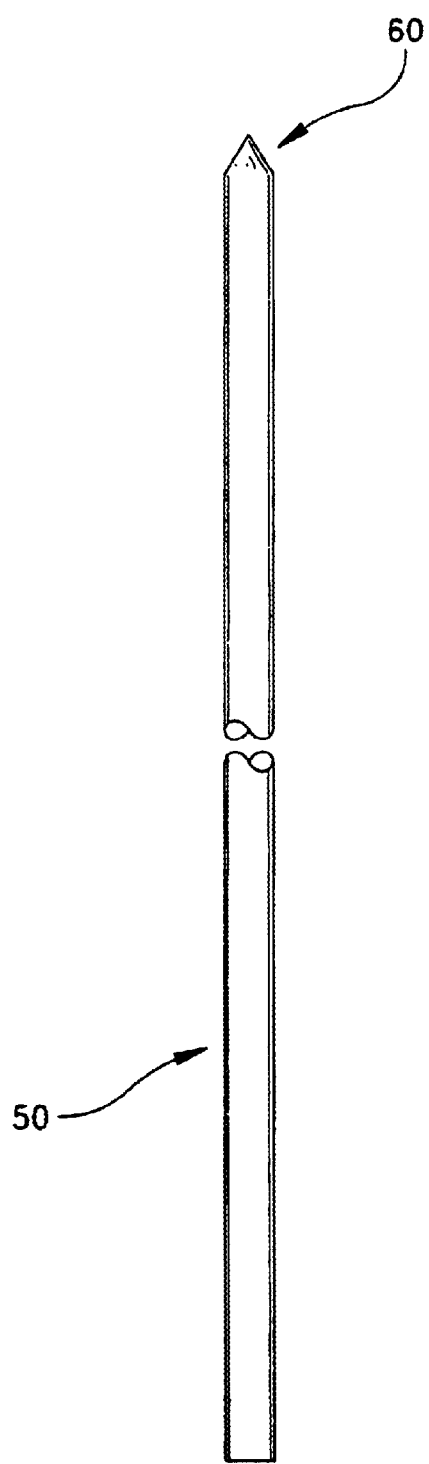
FIG. 10 is a schematic side view of the guidewire used in connection with the present invention.
Figure 11:
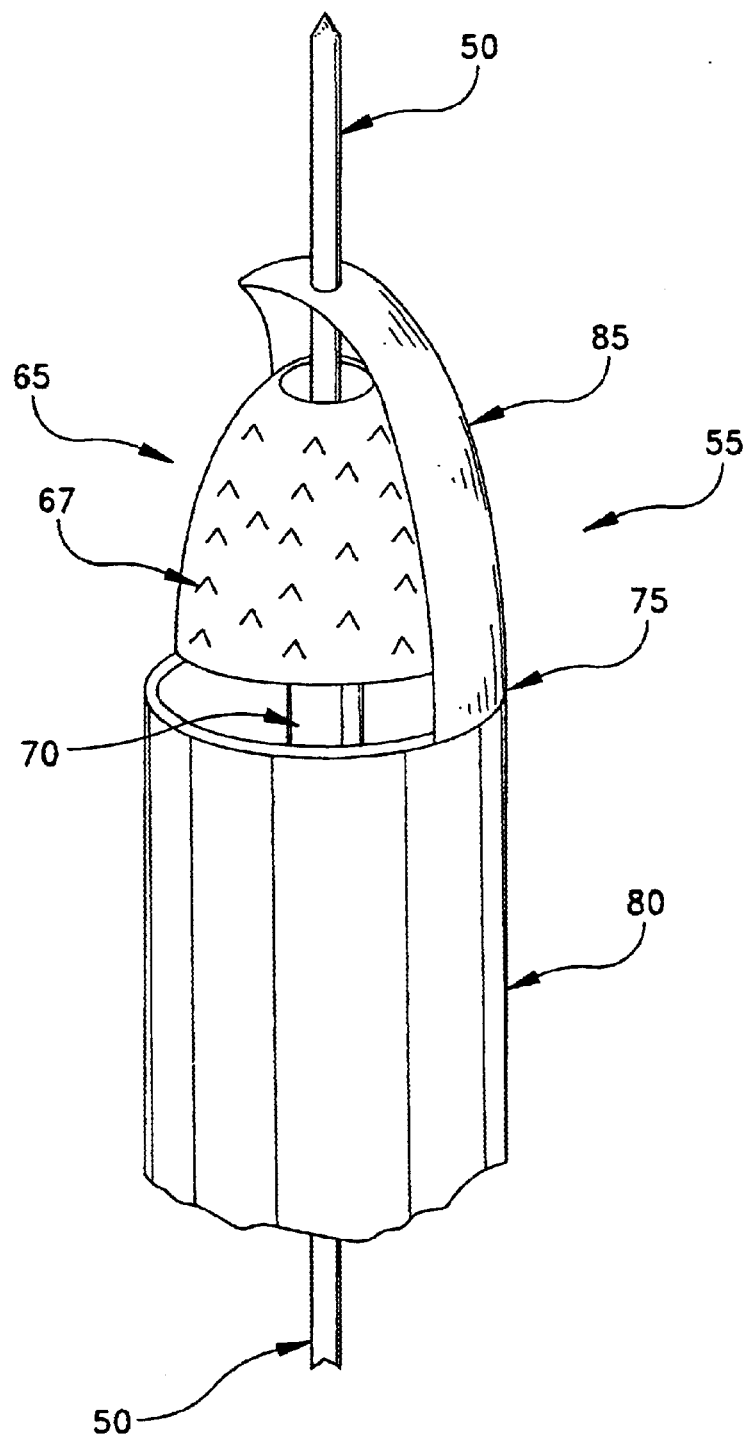
FIG. 11 is a schematic perspective view showing one form of router assembly formed in accordance with the present invention.
Figure 12:
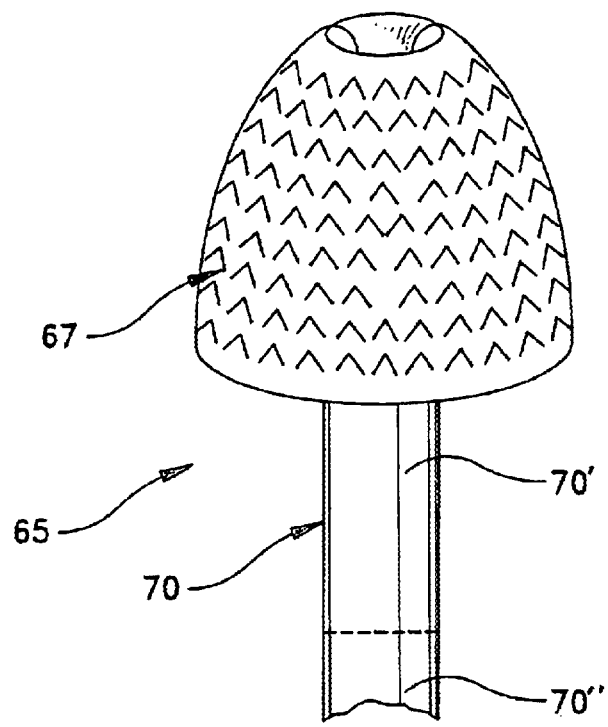
FIG. 12 is a schematic perspective view of the router assembly's cannulated router device.
Figure 13:
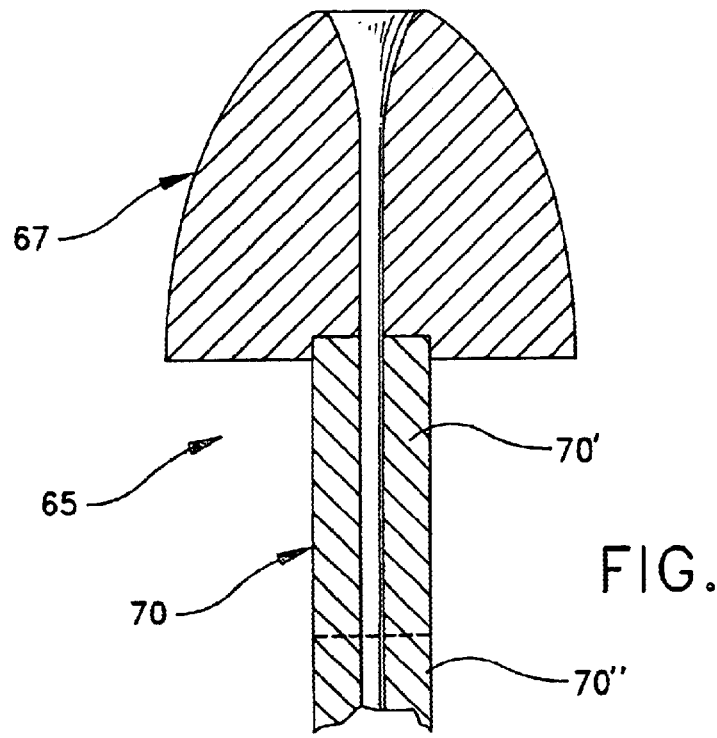
FIG. 13 is a schematic side view, in section, of the cannulated router device shown in FIG. 12.
Figure 14:
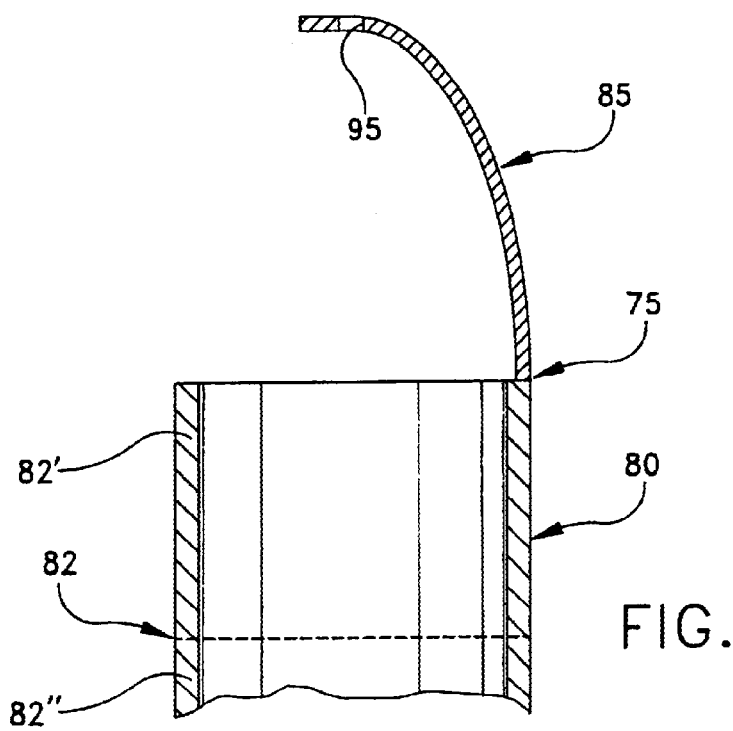
FIG. 14 is a schematic side view, in section, of a portion of the router assembly's shield assembly.

Looking first at FIGS. 10–16, the present invention provides apparatus and a method for removing bone structures from the femoral notch so as to prevent those bone structures from impinging upon a graft ACL installed as part of an ACL reconstruction procedure. The apparatus and method of the present invention are intended to be utilized in an ACL reconstruction procedure aster the damaged ACL has been removed from the knee and after bone tunnel 30 has been formed in tibia 15, but before bone tunnel 35 has been formed in femur 10 and the graft ACL has been positioned in the joint.

Still looking now at FIGS. 10–16, in one preferred embodiment of the present invention, the apparatus of the present invention comprises a guidewire 50 (FIGS. 10 and 11) and a router assembly 55 (FIGS. 11–16).

Guidewire 50 is generally of the sort well known in the art for guiding cannulated elements to a target structure. As such, guidewire 50 includes a sharp point 60 (FIG. 10) on its distal end, whereby the guidewire can be drilled or tapped into a target structure (e.g., femur 10, as will hereinafter be described in further detail). However, unlike other guidewires of the sort known in the art, and in accordance with one preferred embodiment of the present invention, guidewire 50 is preferably formed out of a highly elastic yet firm material. Preferably, guidewire 50 is formed out of a so-called pseudoelastic material, i.e., a "shape memory alloy (SMA)/stress induced martensite (SIM)" material such as Nitinol. By forming guidewire 50 out of such a highly elastic yet firm material, the guidewire has the rigidity needed to penetrate into bone, yet has the high elasticity needed to undergo substantial elastic deformation during joint flexure, as will hereinafter be described in further detail.

Still looking now at FIGS. 11–16, router assembly 55 comprises a cannulated router device 65 (FIGS. 11–13 and 16) which comprises a cannulated cutting head 67 attached to a cannulated shaft 70. At least the distal portion 70' (FIGS. 12, 13 and 16) of cannulated shaft 70 is flexible; the proximal portion 70" of cannulated shaft 70 may or may not be flexible, as desired. On account of this construction, cannulated router device 65 can ride on guidewire 50 as rotary cutting notion is imparted to cutting head 67 by means of shaft 70. In particular, by forming at least the distal portion 70' of cannulated shaft 70 so as to be flexible, router device 65 can ride on guidewire 50 and rotate even as guidewire 50 is subjected to substantial bending during knee joint flexure, as will hereinafter be discussed in further detail.

Router assembly 55 also comprises a shield assembly 75 (FIGS. 11 and 14–16). Shield assembly 75 comprises a body assembly 80 and a hood 85.

Figure 15:
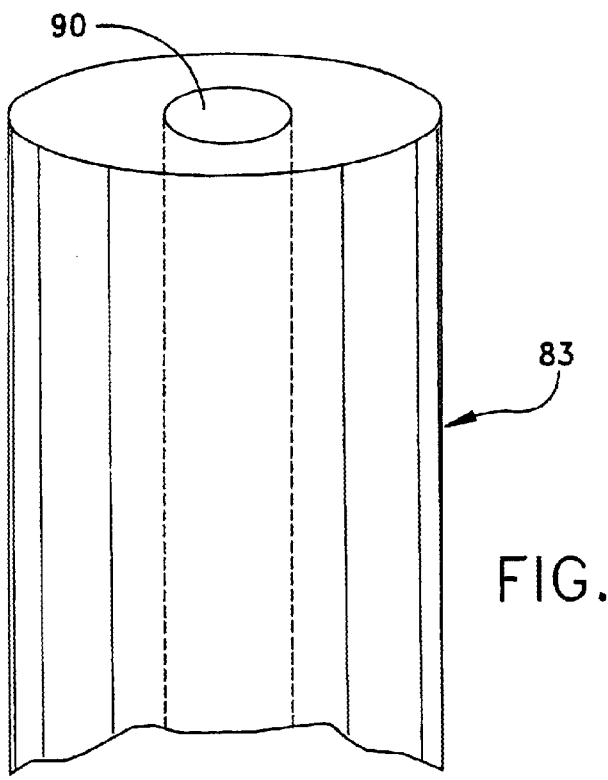
FIG. 15 is a schematic perspective view of the shield assembly's collar.
Figure 16:
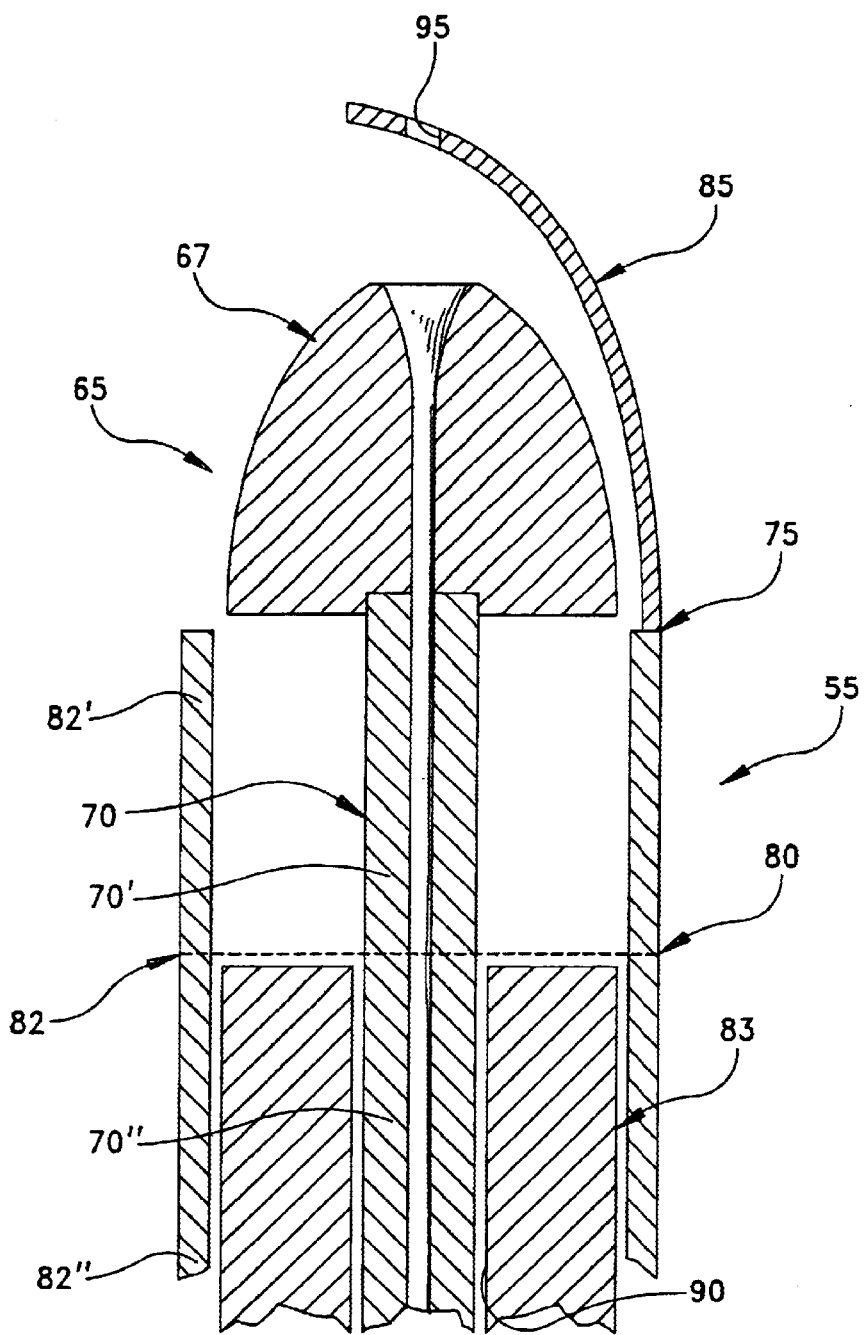
FIG. 16 is a schematic side view, in section, of the router assembly shown in FIG. 11.

Body assembly 80 comprises a hollow outer tube 82 (FIGS. 14 and 16) and an inner collar 83 (FIGS. 15 and 16). At least the distal portion 82' (FIGS. 14 and 16) of hollow outer tube 82 is flexible; the proximal portion 82" of hollow outer tube 82 may or may not be flexible, as desired. Collar 83 is sized and positioned so as to terminate at the juncture of the hollow tube's distal portion 82' and its proximal portion 82" (FIG. 16). Collar 83 includes a hole 90 (FIGS. 15 and 16) for receiving shaft 70 of router device 65. Hole 90 is preferably centered within body 80, whereby the router device's cutting head 67 will be centered within shield assembly 75.

Hood 85 is attached to body 80 and includes a hole 95 (FIGS. 14 and 16) for receiving guidewire 50. Hood 85 surrounds a portion of the router device's cutting head 67 but leaves another portion of the cutting head (i.e., the portion extending outboard or hood 85) exposed for routing operations. By way of example but not limitation, hood 85 might cover approximately ⅔ of the circumferential region surrounding cutting head 67 and leave approximately ⅓ of the circumferential region surrounding cutting head 67 exposed for cutting purposes. Hood 85 may be formed flexible or rigid, as desired.

As a result of this construction, router assembly 55 can ride on guidewire 50 as a unit, with shaft 70 rotating cutting head 67 so as to cut away any material (e.g., impinging bone) exposed to the cutting head, even as hood 85 shields a substantial portion of the cutting head from inadvertently cutting other material (e.g., the patient's PCL). Significantly, due to the flexible nature of shaft portion 70' and tube portion 82', router assembly 55 is able to ride on guidewire 50 even as guidewire 50 is subjected to substantial deformation during knee joint flexure.

Looking next at FIGS. 17–23, guidewire 50 and router assembly 55 are intended to be used as follows.

First, femur 10 and tibia 15 are set at approximately a 90° angle and tibial bone tunnel 30 is formed in tibia 15. Then guidewire 50 is passed through tibial bone tunnel 30 and into femur 10 until the sharp distal end 60 of the guidewire is embedded in the femur, e.g., by drilling or tapping in ways well known in the art (see FIGS. 17 and 18). If desired, a cannulated guide of the sort well known in the art (not shown) may be disposed about guidewire 50 to help stabilize it as it is embedded into femur 10. Guidewire 50 is positioned in the patient so that it will extend along the length where the graft ACL will reside.

Figure 20:
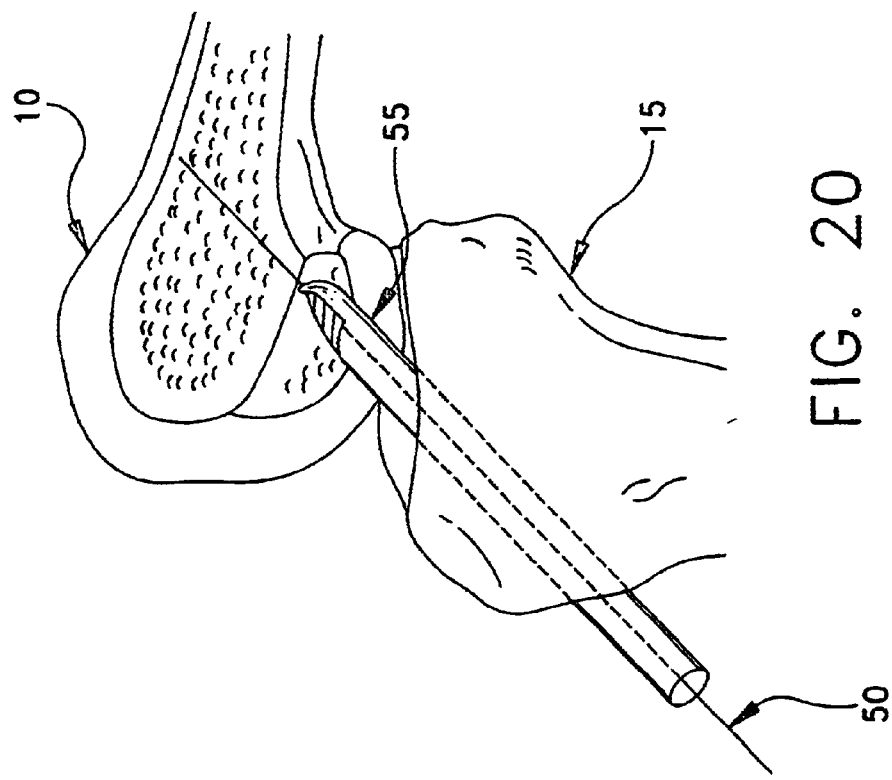
FIG. 20 is a schematic side view showing a router assembly removing lateral bone structures from the femoral notch so as to prevent those lateral bone structures from impinging on a graft ACL.
Figure 19:
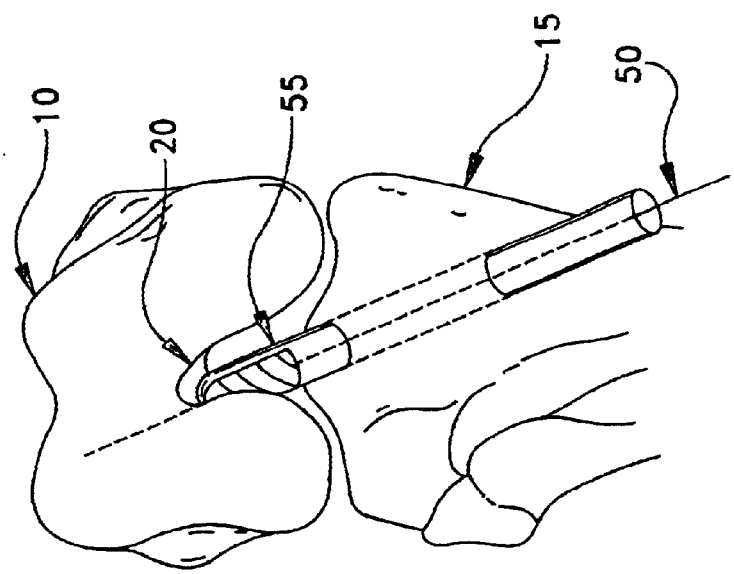
FIG. 19 is a schematic front view like that of FIG. 17, except showing a router assembly removing lateral bone structures from the femoral notch so as to prevent those lateral bone structures from impinging on a graft ACL.

Next, router assembly 55 is loaded onto the proximal end of guidewire 50 and moved down into the interior of the knee joint so that the router assembly's cutting head 67 is in the vicinity of femoral notch 20 (see FIGS. 19 and 20). Then body 80 of router assembly 55 is turned so that the router assembly's cutting head 67 is directed toward the impinging portions of the femur which are to be removed, and so that the router assembly's protective hood 85 is placed between the cutting head and the PCL so as to protect the PCL from the cutting head. Then shaft 70 is rotated, e.g., with a power driver (not shown) of the sort well known in the art, so as to rotate cutting head 67 and thereby cut away any anatomical structures it comes into contact with.

By turning body 80 circumferentially as required, cutting head 67 can be used to enlarge femoral notch 20 while keeping the cutting head from engaging (and thereby cutting) the PCL and/or other sensitive anatomical structures. In particular, by turning router assembly 55 so that it faces in the manner shown in FIGS. 19 and 20, lateral notch structures can be removed. Similarly, by turning router assembly 55 so that it faces in the manner shown in FIGS. 21 and 22, roof notch structures can be removed.

Significantly, the impinging bone can be removed quickly, easily and safely, without direct visualization of the anatomical structures being trimmed away, due to the use of guidewire 50 and the guidewire-following router assembly 55.

In particular, it is to be appreciated that, by positioning guidewire 50 so that it will extend along the length where the graft ACL will reside, and by properly sizing the radial dimensions of router assembly 55 relative to the graft ACL which will thereafter be installed, the router assembly will clear away only as much bone as is required to properly size the femoral notch and eliminate impingement problems. Furthermore, by properly sizing the longitudinal dimensions of router assembly 55 relative to the notch region where impingement occurs, impingement can be eliminated by just circumferential movement of router assembly 55 on guidewire 50, i.e., without requiring longitudinal movement of router assembly 55 on guidewire 50 during bone-trimming operations.

Figure 22:
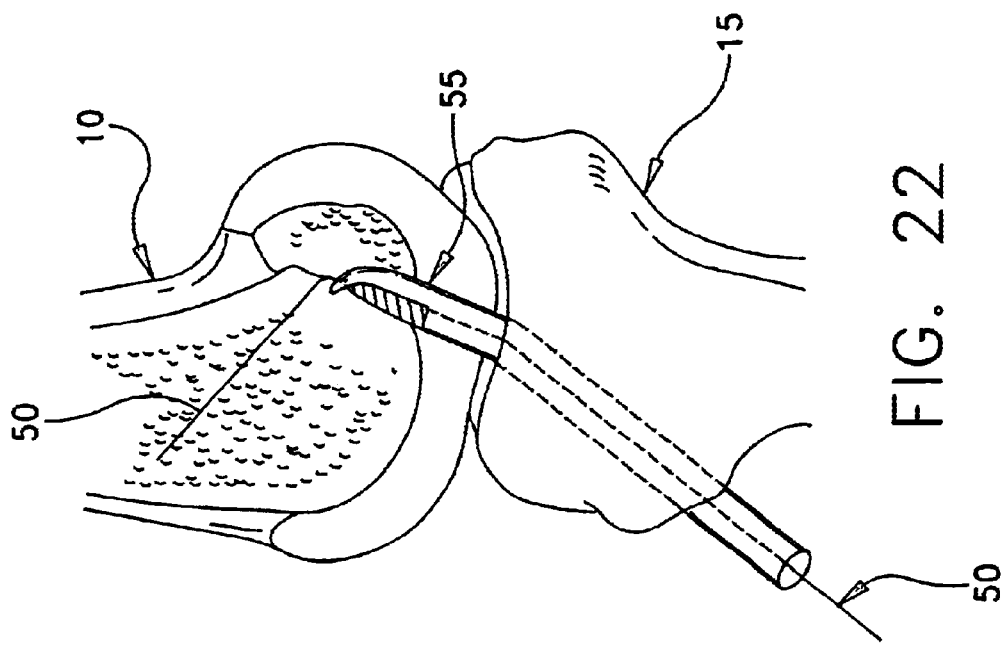
FIG. 22 is a schematic side view of the knee and router assembly shown in FIG. 21.
Figure 21:
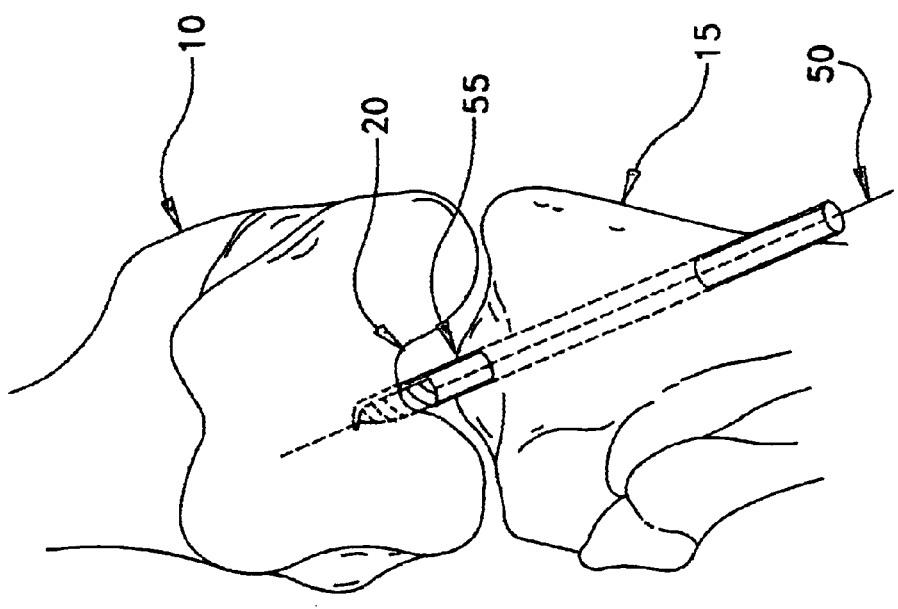
FIG. 21 is a schematic front view, showing the leg substantially straight and the router assembly removing roof bone structures from the femoral notch so as to prevent those roof bone structures from impinging on a graft ACL.
Figure 23:
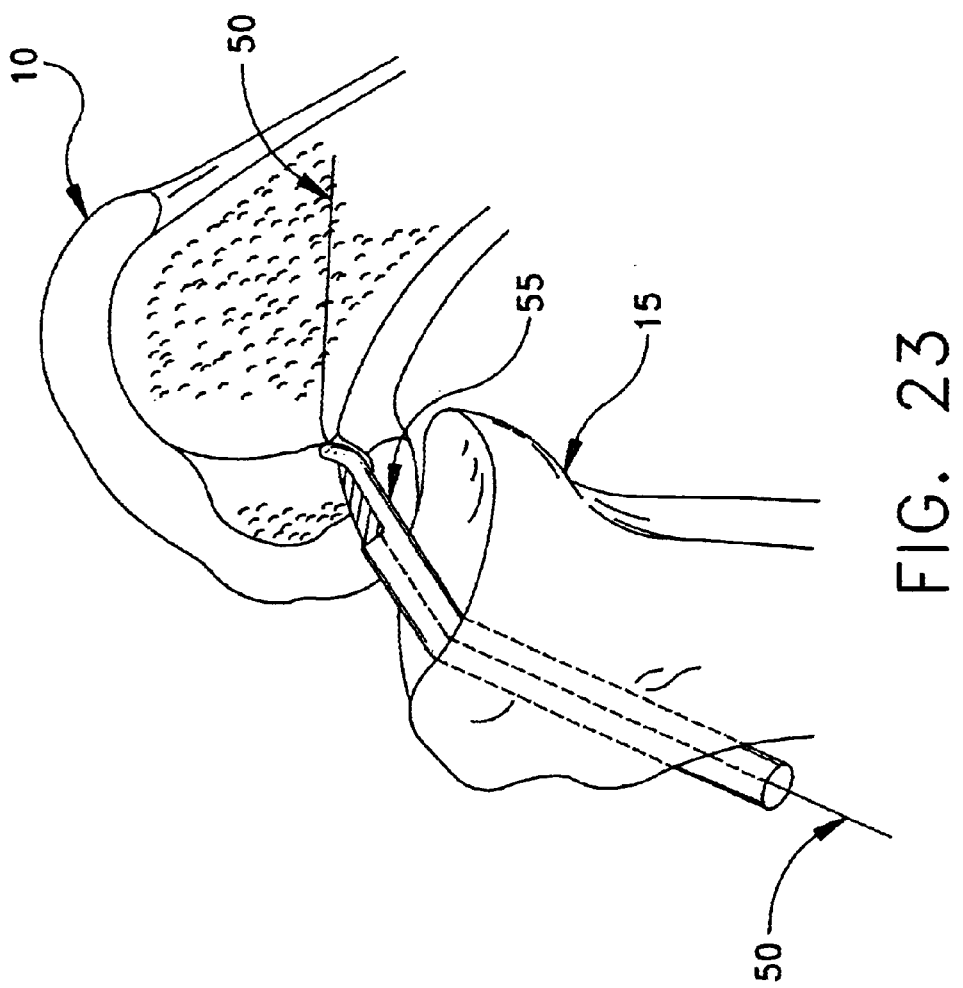
FIG. 23 is a schematic side view, showing the knee flexed at approximately a 140° angle and the router assembly removing bone structures from the femoral notch so as to prevent those bone structures from impinging on a graft ACL.

Significantly, since guidewire 50 is preferably formed out of a highly elastic material, and since the router assembly's shaft portion 70' and body portion 82' are formed so as to be flexible, it is possible to use router assembly 55 to remove impinging bone in a dynamic sense, i.e., to use the router assembly to cut away impinging bone even as the knee is flexed through a full range of natural motions. See, for example, FIGS. 19 and 20, where router assembly 55 is shown enlarging the femoral notch while the patient's leg is bent at approximately a 90° angle; FIGS. 21 and 22, where router assembly 55 is shown enlarging the femoral notch while the patient's knee is substantially straight; and FIG. 23, where router assembly 55 is shown enlarging the femoral notch while the patient's knee is bent at approximately a 140° angle. It should be noted in FIGS. 21 and 22, and again in FIG. 23, how guidewire 50 and router assembly 55 are capable of undergoing substantial elastic Wok deformation during such knee flexing even as bone-trimming operations are under way.

Figure 24:
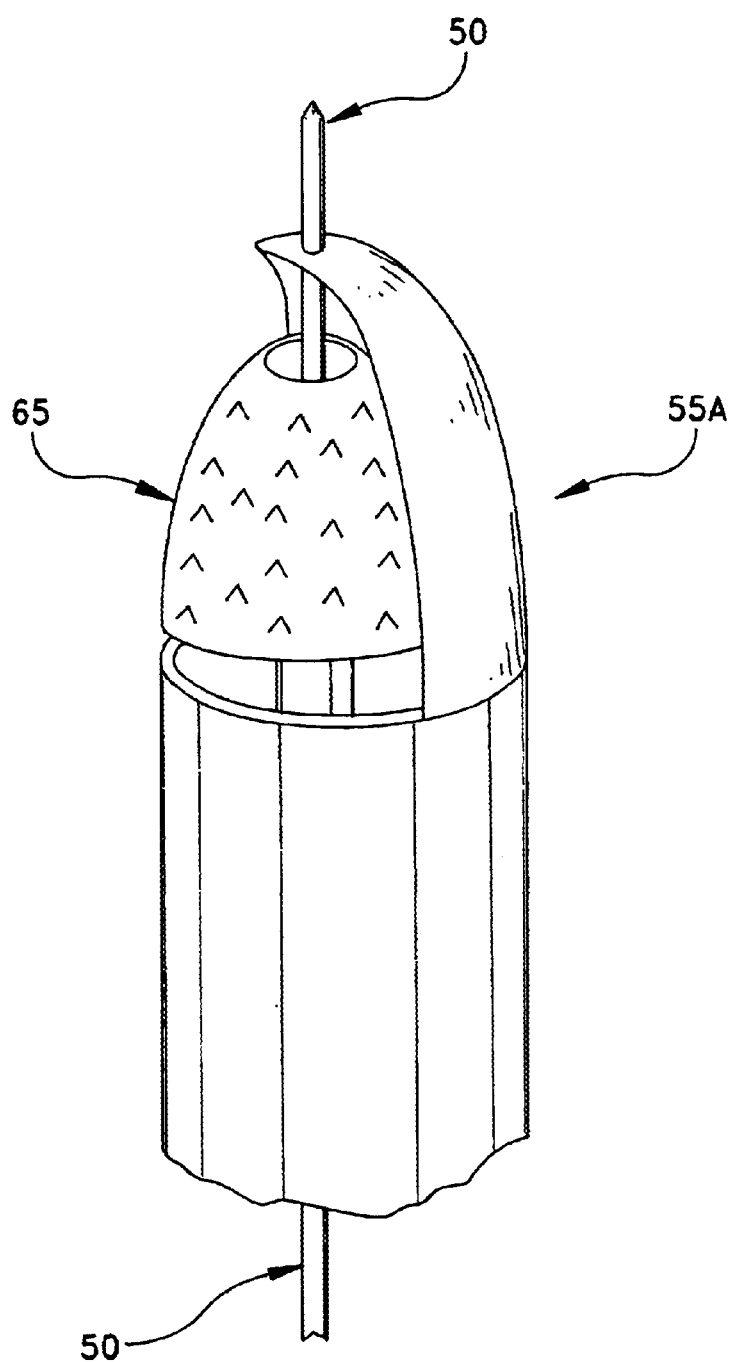
FIG. 24 is a schematic perspective view showing an alternative form of router assembly formed in accordance with the present invention.
Figure 25:
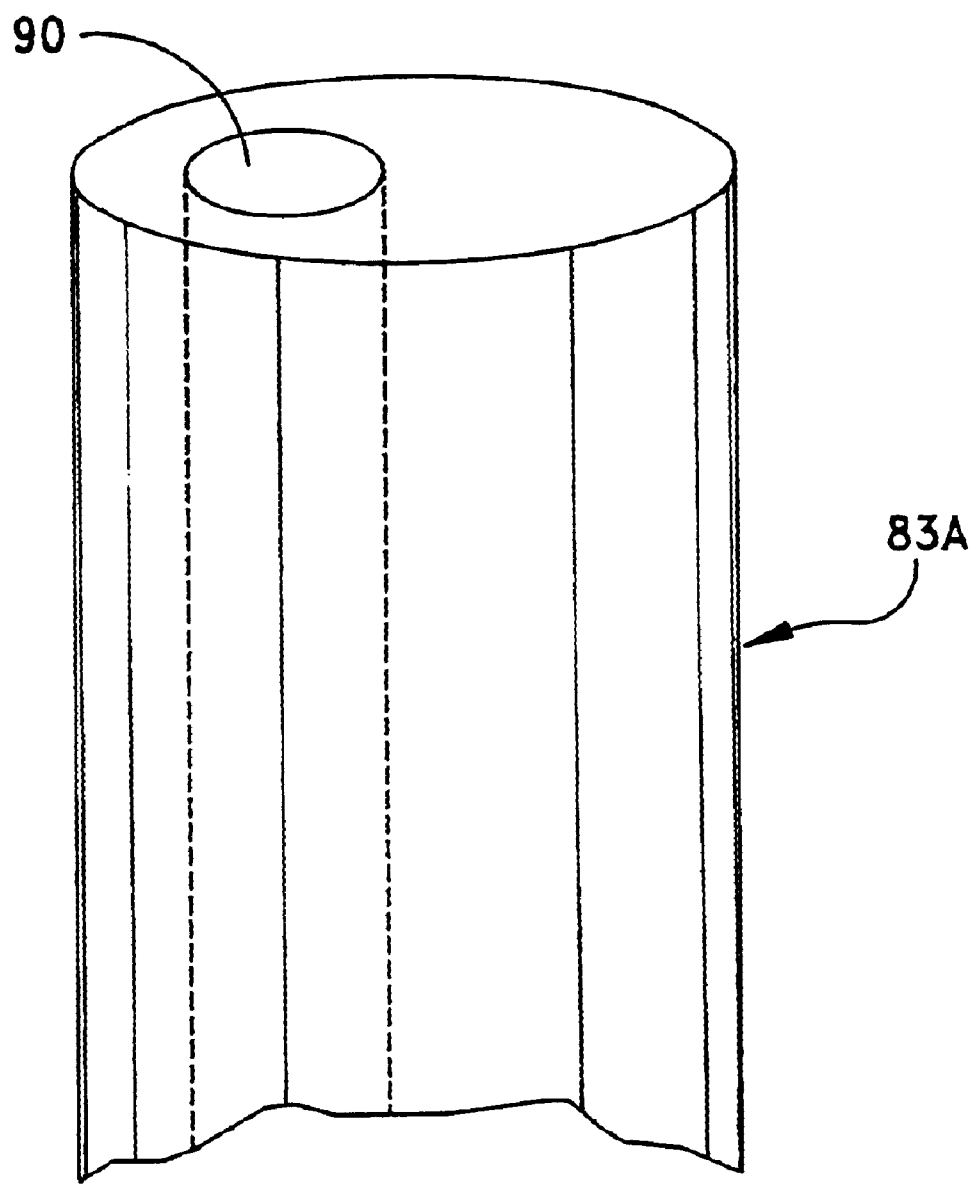
FIG. 25 is a schematic perspective view showing the collar used in connection with the router assembly shown in FIG. 24.
Figure 26:
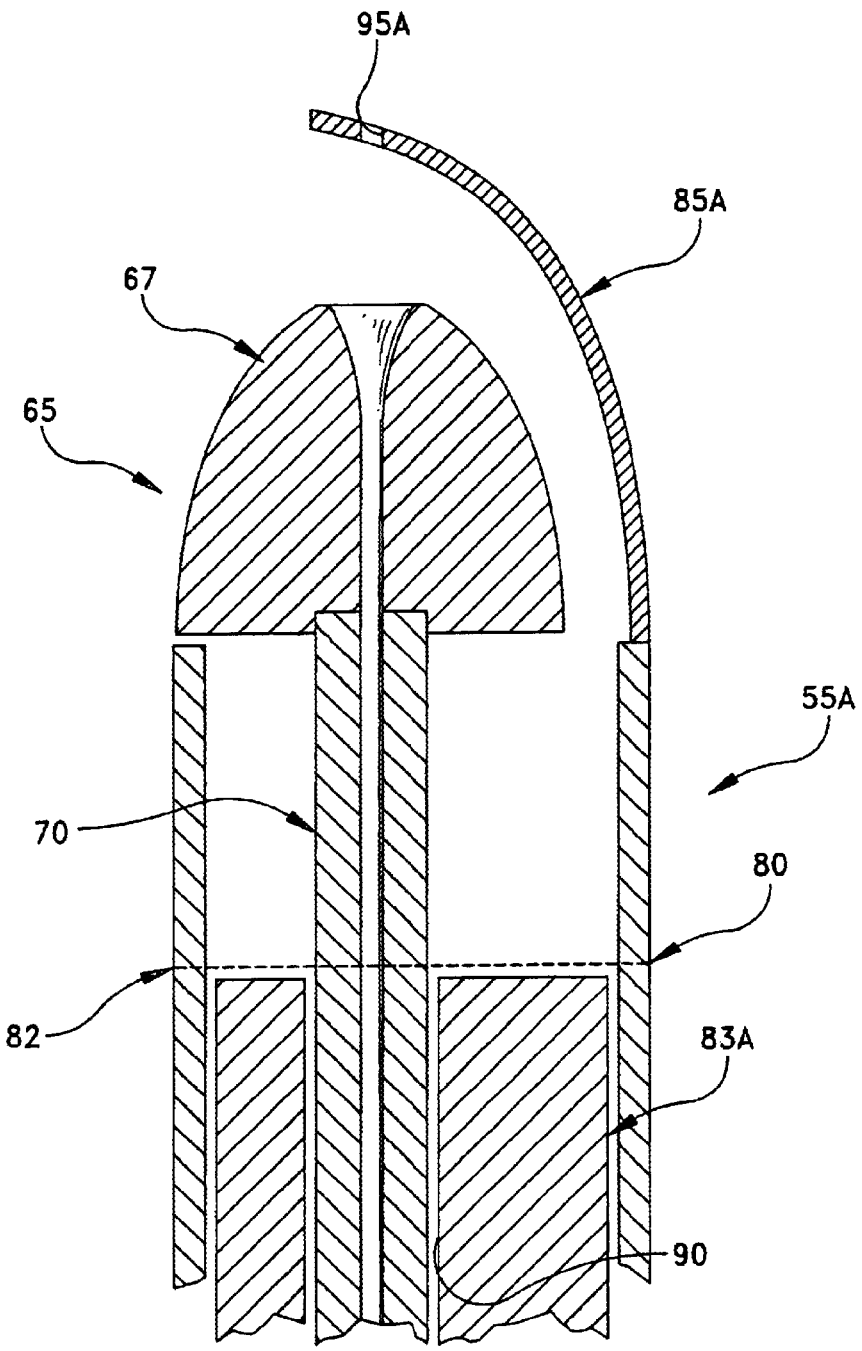
FIG. 26 is a schematic side view, in section, of the router assembly shown in FIG. 24.

Looking next at FIGS. 24–26, in another preferred embodiment of the present invention, the apparatus of the present invention comprises guidewire 50 and a router assembly 55A.

Router assembly 55A is substantially the same as router assembly 55 described above, except as is shown in the drawings and/or hereinafter described. In particular, router assembly 55A utilizes a collar 83A (FIGS. 25 and 26) rather than the collar 83 described above. Collar 83A has its hole 90 disposed off-center within the collar, whereby the router device's cutting head 67 will be clocked to one side relative to the body's hollow outer tube 82 (see FIG. 26). In particular, with router assembly 55A, collar 83A is arranged so that the router device's cutting head 67 is clocked outboard relative to the central axis of hollow outer tube 82. This permits the router device to engage impinging bone more readily. In order to accommodate such lateral displacement of router device 65, the router assembly's hood 85A has its hole 95A shifted laterally as well, in the manner shown in FIG. 26.

In operation, router assembly 55A is intended to be used in substantially the same way as router assembly 55.

Figure 27:
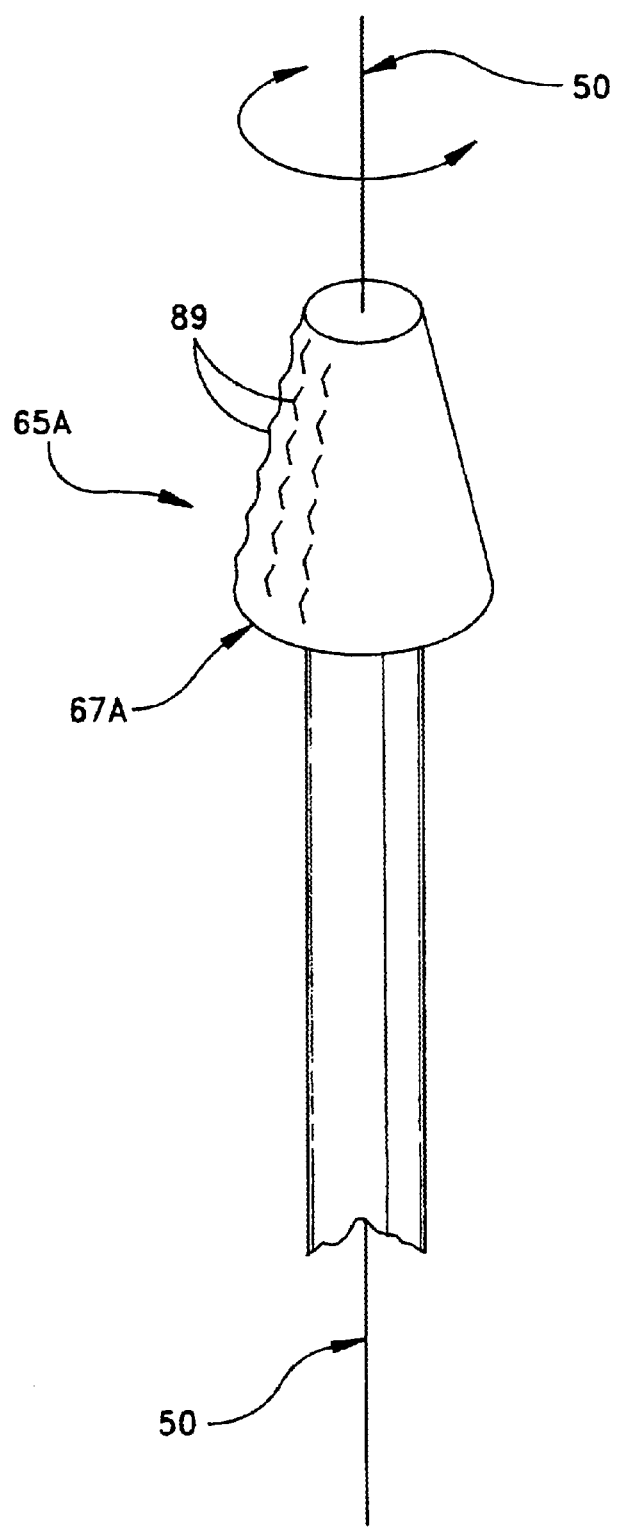
FIG. 27 is a schematic perspective view of another form of router device which can be used in connection with the present invention.

Looking next at FIG. 27, in another preferred embodiment of the present invention, the apparatus of the present invention comprises guidewire 50 and a cannulated router device 65A. Router device 65A is generally similar to the router device 65 discussed above, except that with router device 65A, its cutting teeth 89 are disposed about only a portion of the periphery of its cutting head 67A, with the remainder of the cutting head being smooth and non-abrasive. Accordingly, by moving cannulated router device 65A on guidewire 50 so as to oscillate the router device through only a fraction of a complete revolution, bone can be removed adjacent to the cutting teeth 89 while the remainder (i.e., the non-cutting portion) of the cutting head 67A safely opposes any delicate structures Which are to be safeguarded (e.g., the PCL). Thus, with the apparatus of FIG. 27, impinging bone may be safely removed without providing a shield assembly (e.g., such as the shield assembly 75 described above) for the router device.

Figure 28:
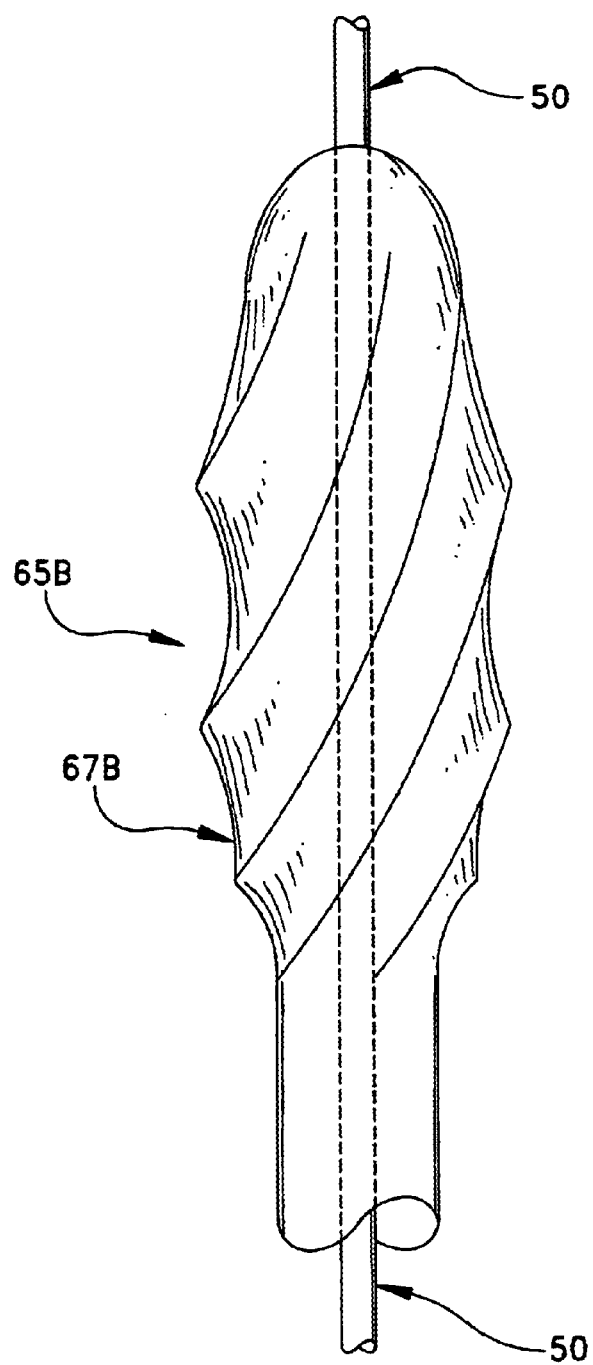
FIG. 28 is a schematic perspective view of yet another form of router device which can used in connection with the present invention.

In another form of the invention, the cannulated router device 65A of FIG. 27 could be replaced with a cannulated router device of the sort adapted to remove hard bone while leaving soft tissue unharmed. By way of example, the cannulated router device 65A of FIG. 27 might be replaced by the cannulated router device 65B shown in FIG. 28. More particularly, router device 65B includes a cutting head 673 having an outer configuration similar to that disclosed in U.S. Pat. No. 4,445,509 issued May 1, 1984 to David C. Auth for METHOD AND APPARATUS FOR REMOVAL OF ENCLOSED ABNORMAL DEPOSITS, which patent is hereby specifically incorporated herein by reference. Alternatively, cutting head 67B could have some other configuration of the sort well known in the art which permits cutting of hard bone without harming soft tissue. As a result of such a construction, a cannulated router device 65B having such a configuration could then be safely rotated completely about guidewire 50 so as to remove impinging bone without risking damage to delicate soft tissue. Thus, with the apparatus of FIG. 28 or with equivalent cutting apparatus, impinging bone can be safely removed without providing a shield assembly (such as the shield assembly 75 described above) for the router device.

The foregoing apparatus may be used in an ACL reconstruction procedure as follows. First, the patient's knee is extended at an angle of approximately 90°. Then, a bone tunnel 30 is formed in the tibia in ways well known in the art. Next, guidewire 50 is passed through bone tunnel 30 and up into the femur. Then a cannulated router device (in the form of either router assembly 55, or router assembly 55A, or router device 65A, or router device 65B) is loaded onto guidewire 50 and used to perform the desired notchplasty in the manner previously described. Next, the cannulated router device is dismounted from guidewire 50. Then bone tunnel 35 is formed in femur 10 in ways well known in the art. Then guidewire 50 is removed from femur 10. Finally, a graft ACL 5A is installed in femoral bone tunnel 35 and tibial bone tunnel 30 in ways well known in the art.

Figure 29:
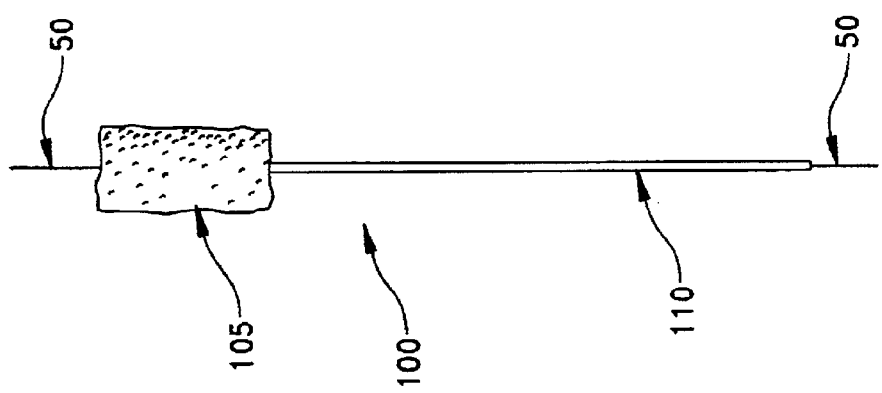
FIG. 29 is a schematic side view of a cannulated marking device formed in accordance with the present invention.

Looking next at FIG. 29, in another preferred embodiment of the present invention, the apparatus of the present invention comprises guidewire 50 and a marking device 100. Marking device 100 preferably comprises a resilient cannulated head 105 and a flexible cannulated shaft 110 connected to head 105. Cannulated head 105 is formed so that it can hold and release a dye without cutting bone. Marking device 100 is used by moving the device up and down guidewire 50, with or without rotation, whereby the marking head 105 will contact any bone in its way. By sizing marking device 100 properly relative to the size of the graft ACL which is to be installed, movement of marking device 100 along guidewire 50 while the knee is moved through a range of natural motions will cause the marking element to leave its dye on any portions of the femur which might impinge upon the graft ACL which will thereafter be installed in the knee. Thereafter, marking device 100 and guidewire 50 are removed from the surgical site and the surgeon may utilize a conventional cutting element to remove the marked bone. Then the graft ACL may be installed in the knee without fear of impingement.

In the foregoing description of the preferred embodiments of the invention, it was noted that guidewire 50 is preferably formed out of a pseudoelastic material so as to provide the desired characteristics of firmness and flexibility. However, it should also be appreciated that a guidewire made out of a non-pseudoelastic material can also be utilized in connection with the present invention. Of course, inasmuch as the preferred use of the present invention involves flexing the knee over a wide range of motions with the guidewire in place, limitations in wire flexibility can inhibit the range of knee movements performed with the guidewire in place. Thus, in the situation where a non-pseudoelastic guidewire is to be used, it can be helpful to mount the distal end of the guidewire in a fixture by means of a universal joint. This fixture can then be attached to the bottom surface of the femur or, more advantageously, it can be disposed in a bore formed in the bottom of the femur. Preferably this bore is the femoral bone tunnel 35 used for the ACL reconstruction procedure.

Figure 30:
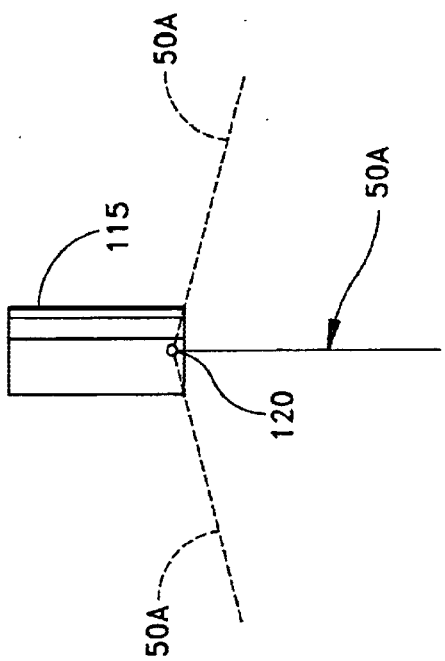
FIG. 30 is a schematic side view of a novel type of guidewire assembly formed in accordance with the present invention.

More particularly, and looking now at FIG. 30, the distal end of a non-pseudoelastic guidewire 50A can be mounted in a fixture 115 by a universal joint 120 whereby the proximal end of the guidewire can move about relative to fixture 115. As a result of this construction, when fixture 115 is positioned in the femoral bone tunnel, universal joint 120 will help guidewire 50A to accommodate the degree of deformation required as the knee is moved through a full range of natural motions. Of course, with this embodiment of the invention, the femoral bone tunnel 35 must be formed before the notchplasty procedure is performed, since fixture 115 is intended to be received in bone tunnel 35.

Modifications of the Preferred Embodiments

It is to be appreciated that modifications may be made to the preferred embodiments described and illustrated above without departing from the scope of the present invention Thus, for example, while in the foregoing description the present invention has been described in the context of reconstructing an ACL, it should also be appreciated that the present invention has application to the reconstruction of other ligaments as well, where similar impingement problems can occur. Thus, for example, the present invention might be used in connection with reconstructing the posterior cruciate ligament (PCL).

The present invention can also be used to clear away impinging structures in other anatomical and non-anatomical settings.

Advantages of the Invention

Numerous advantages are achieved through the use of the present invention.

For one thing, the present invention provides improved apparatus for reconstructing a ligament.

And the present invention provides improved apparatus for reconstructing an anterior cruciate ligament (ACL).

Also, the present invention provides improved apparatus for quickly, easily and reliably eliminating impingement problems when reconstructing an anterior cruciate ligament.

And the present invention provides improved apparatus for quickly, easily and reliably removing any anatomical structures (e.g., bone) which will conflict with the location of a graft ACL at the completion of an ACL reconstruction procedure.

The present invention also provides improved apparatus for quickly, easily and reliably removing any anatomical structures (e.g., bone) which will conflict with the location of a graft ACL as the knee is moved through a full range of natural motions.

The present invention also provides an improved method for reconstructing a ligament.

And the present invention provides an improved method for reconstructing an anterior cruciate ligament (ACL).

And the present invention provides an improved method for quickly, easily and reliably eliminating impingement problems when reconstructing an anterior cruciate ligament.

Also, the present invention provides an improved method for quickly, easily and reliably removing any anatomical structures (e.g., bone) which will conflict with the location of a graft ACL at the completion of an ACL reconstruction procedure.

And the present invention provides an improved method for quickly, easily and reliably removing any anatomical structures (e.g. bone) which will conflict with the location of a graft ACL as the knee is moved through a full range of natural motions.

What is claimed is:

1. A method for removing portions of a bone, said method comprising the steps of:

providing (i) a guidewire, and (ii) a router assembly comprising a cutting head fixed to a shaft rotatably disposed in a hole through a body portion of a shield assembly, and a hood portion of said shield assembly extending from said body portion of said shield assembly and covering a first portion of said cutting head while leaving exposed a second portion of said cutting head, said shaft and said cutting head having bores therethrough, and said shield assembly hood portion having a hole therein;

pivotally connecting a distal end of the guidewire to a fixture;

anchoring the fixture in a tunnel in the bone to thereby anchor the guidewire in the bone;

mounting said router assembly on said guidewire such that said guidewire extends through said shaft bore, said cutting head bore, and said hood portion hole, and moving said router assembly along said guidewire to proximate the bone; and positioning said router assembly such that said second portion of said cutting head is directed toward the bone portion to be removed, and rotating said shaft, to rotate said cutting head, to remove portions from the bone, while the shield assembly hood portion separates said cutting head from other anatomical structures.

* * * * *